(12) United States Patent
Robinson et al.

(10) Patent No.: US 8,828,449 B2
(45) Date of Patent: Sep. 9, 2014

(54) WOUND DRESSING COMPOSITION AND METHOD OF USE

(71) Applicants: Libby Robinson, Memphis, TN (US); Mikel Hays, Irving, TX (US)

(72) Inventors: Libby Robinson, Memphis, TN (US); Mikel Hays, Irving, TX (US)

( * ) Notice: Subject to any disclaimer, the term of this patent is extended or adjusted under 35 U.S.C. 154(b) by 43 days.

(21) Appl. No.: 13/644,024

(22) Filed: Oct. 3, 2012

(65) Prior Publication Data

US 2013/0195999 A1    Aug. 1, 2013

Related U.S. Application Data

(60) Provisional application No. 61/590,946, filed on Jan. 26, 2012.

(51) Int. Cl.
*A61K 33/00* (2006.01)

(52) U.S. Cl.
USPC ........... 424/600; 424/642; 424/602; 424/606; 424/610; 424/614; 424/722

(58) Field of Classification Search
CPC ...... A61K 33/30; A61K 33/10; A61K 33/106
See application file for complete search history.

(56) References Cited

U.S. PATENT DOCUMENTS

| 6,149,947 A | 11/2000 | Hon et al. |
| 6,277,388 B1 * | 8/2001 | Chevalier ...................... 424/401 |
| 2003/0036490 A1 * | 2/2003 | Lorant et al. .................. 510/130 |
| 2013/0047347 A1 * | 2/2013 | Smith et al. ....................... 8/161 |

OTHER PUBLICATIONS

Lelbanc, M.M., Rood and Riddle Equine Hospital, Lexington, KY; J. ANim. Sci. vol. 88, E-Suppl. 2/JDiary Sci. vol. 93, E-Suppl. 1/Poult. Sci. vol. 89, E-Suppl. I, 2010.
Ryan, P.L. et al.; Monitoring pathogen progression during uterine infection in the mare using biophotonic imaging technology and lux-modified bacteria; J. Anim. Sci, vol. 88, 2010.
Leblanc, M.M.; Reproduction inDomestic Animals; advances in the diagnosis and Treatment of Chronic Infectious and Post-Mating Induced Endometritis inthe Mare; Reprod. Dom A, 2010.

* cited by examiner

*Primary Examiner* — Lezah Roberts
*Assistant Examiner* — Nannette Holloman
(74) *Attorney, Agent, or Firm* — Harris, Shelton, Hanover & Walsh; Susan B. Fentress

(57) ABSTRACT

The present invention provides a non-irritating, sprayable wound dressing composition and a non-irritating, non-sprayable ointment for treating wounds in mammals such as horses or dogs. The composition of the present invention is made of an acceptable carrier and an active ingredient made of organic salts of naturally occurring cations having the capacity to facilitate healing of wounds.

17 Claims, No Drawings

WOUND DRESSING COMPOSITION AND METHOD OF USE

RELATED PATENT APPLICATIONS

This patent application claims the benefit of U.S. provisional patent application Ser. No. 61,590,946 filed on Jan. 26, 2011 under 35 USC sec 119 (e) (hereby specifically incorporated by reference).

BACKGROUND OF THE INVENTION

1. Field of the Invention

This invention relates to wound dressing composition; particularly, those formulated into a non-irritating ointment and a non-irritating spray.

2. Description of the Prior Art

Normal healing requires a balancing act between the removal of dead tissue and the construction of new tissue. This involves a precise interaction between numerous cell types, as well as growth factors, enzymes and cytokines for normal healing to proceed. The normal healing process should proceed as in the diagram below. Chronic wounds are due to an imbalance in the healing process. Matrix metalloproteinases (MMP) and their inhibitors, (tissue inhibitors of metalloproteinases (TIMPs)) are key for this process to occur in the animals/mammals as well as the human.

In the normally healing wound, various MMPs are expressed throughout the healing process. In chronic wounds, MMP/TIMP imbalances decrease healing. Naturally occurring cations, such as Potassium, Rubidium, Calcium, and Zinc, have been shown to regulate protease imbalances, down-regulate the production of reactive oxygen species (ROS) which can damage other molecules and the cell structures of which they are a part, and stimulate re-epithelialization.

U.S. Pat. No. 6,149,947 issued to Hon describes a composition for providing therapeutic efficacy for wound healing containing Potassium, Rubidium, Zinc and Calcium ions, in combination with suitable inorganic salts. The Hon synthetic formulations contain by weight of inorganic solids, 10 to 80 parts potassium ions, but preferably 30 to 50 parts potassium ions.

A water-miscible ointment based product based on Hon causes a subjective irritation of some animals when applied to their wounds. This irritation is observed as a reluctance of the animal to remain still or quickly try to remove the applied treatment. In the case of large animals, e.g. a horse, this can create a dangerous situation for the animal-care professional, e.g. a veterinarian. A need exists to provide a wound healing compound that is both efficacious and acceptable to the subject in need of treatment.

BRIEF SUMMARY OF THE INVENTION

The present invention overcomes these limitations by providing both ointment and spray formulas that are less irritating, i.e. better tolerated by subjects, such as animals. The composition provided is made of an acceptable carrier and an active ingredient. The active ingredient includes naturally occurring cations that facilitate healing of wounds associated with organic counter anions, e.g. acetate, citrate, gluconate, to form an acidic composition. The naturally occurring cations, used to facilitate healing of chronic wounds contemplated by this invention include: Potassium, Rubidium, Zinc, Calcium and Sodium. Furthermore, a method to treat wounds using a non-irritating ointment or spray is provided herein.

DETAILED DESCRIPTION OF THE INVENTION

The present invention provides a sprayable wound dressing composition and non-irritating non-sprayable ointment for treating wounds in mammals, such as horses or dogs. The composition of the present invention is made of an acceptable carrier and an active ingredient. The active ingredient is made of organic salts of naturally occurring cations that facilitate healing of wounds. The substitution of organic salts of potassium, rubidium, calcium, and zinc, combined with the addition of an organic salt of sodium and increasing the pH in the range of between 5-7, provides a composition that cause less subjective irritation, when applied to a wound of the mammalian subject.

The naturally occurring cations used to facilitate healing of wounds contemplated by this invention include Potassium, Rubidium, Zinc, Calcium and Sodium. The preferred weight percent of Potassium ranges from 0.64 to 1.55 percent of the wound dressing composition, Sodium ranges from 0.016 to 0.019 percent of the wound dressing composition, Rubidium ranges from 0.005 to 0.022 percent of the wound dressing composition, Calcium ranges from 0.0001 to 0.0025 percent of the wound dressing composition, and Zinc ranges from 0.00008 to 0.0003 percent of the wound dressing composition. The active ingredient, such as naturally occurring cations, is associated with organic anions, such as acetate, hydrogen citrate, dihydrogen citrate ion, tribasic citrate ion, and gluconate ion.

The acceptable carrier includes water and a water-miscible glycol solvent in a ratio to obtain the desired end product, either a spray or an ointment. In the preferred embodiment, the water-miscible glycol solvent is Polyethylene glycol (PEG) or PEG derivatives, thereof such as alpha.omega.-dihydroxy-PEG or .alpha.,omega.-diamino-PEG. Other suitable water-miscible glycol solvents include polypropylene glycol and peroxide-free polyethylene glycol having a molecular weight in the range of 200-600. See U.S. Pat. No. 4,213,979, entitled, "A cosmetically elegant and stable topical anti-inflammatory and antipruritic hydrocortisone solution, stabilized for use in a non-aerosol spray assembly with PPG-12-PEG-50-Lanolin."

If an ointment is desired the weight ratio of the acceptable carrier, between water and PEG, is 3:1, while if a spray is desired the ratio of PEG to water is 1:1.

The pH of the solution can be targeted for a specific pH by adding various amounts of organic acids, e.g. citric or gluconic, with their counter ions, e.g. citrate and gluconate.

In the preferred embodiment, the composition is formulated as a spray, as this can be advantageously applied to large mammals, such as horses, that are in need of treatment. However, the formulation of the spray requires that the active ingredients do not run off when applied to the treatment area. More specifically, as moisture is evaporated from the spray, the composition forms the consistency of an ointment and thus provides the benefits of extended contact with the wound. The preferred formulation is particularly suited for use in a pump spray device as formulations containing 4 weight percent of organic salts and 96 weight percent of an acceptable carrier.

The formulation can be utilized in conjunction with any non-aerosol spray assembly. Many such spray assemblies are widely known and used, such as the squeeze spray assembly shown in U.S. Pat. Nos. 3,361,304 and 3,474,936 (which are herein incorporated by reference), or the pump spray system shown in U.S. Pat. Nos. 4,010,874 and 4,022,354 (which are also herein incorporated by reference). The spray assembly will generally include a reservoir for holding the sprayable composition; a mechanism for mixing the composition with air; and a mechanism to dispense the air/liquid mixture as a spray. This is usually accomplished by creating a pressure differential between the atmosphere and the inside of the container, e.g. a pumper or squeezing a resilient container wall.

Compositions made of an acceptable carrier and an active ingredient including naturally occurring cations to facilitate healing of wounds associated with organic anions to form an acidic solution are shown in Tables 1 and 2.

TABLE 1

FORMULA, OINTMENT & SPRAY NONIRRITATING

| Component | Units | C OINTMENT | D SPRAY |
|---|---|---|---|
| Water | kg | 24.00 | 40.00 |
| H3Cit | kg | 0.20 | 0.40 |
| K3Cit•H2O | kg | 2.15 | 4.00 |
| KCl | kg | 0.00 | 0.00 |
| KOH (as needed for pH) | kg | 0.00 | 0.00 |
| RbC2H3O2 | g | 10.00 | 43.00 |
| Ca3Cit2•4H2O | g | 0.65 | 11.00 |
| Zn3Cit2•2H2O | g | 0.30 | 1.00 |
| Na3Cit•2H2O | g | 81.00 | 77.00 |
| Benzoic Acid | g | 120.00 | 120.00 |
| PEG 400 | kg | 37.00 | 27.00 |
| PEG 4000 | kg | 45.00 | 31.00 |
| Total Batch Mass (calculated) | kg | 108.56 | 102.65 |
| Total Batch Volume (estimated) | L | 30 | 30 |
| K+, total | g | 777 | 1446 |
| [K+], (in Total Batch Mass) | ppm | 7161 | 14089 |
| Rb+, total | g | 5.91 | 25.43 |
| [Rb+], (in Total Batch Mass) | ppm | 54 | 248 |
| Ca2+, total | g | 0.1370 | 2.3183 |
| [Ca2+], (in Total Batch Mass) | ppm | 1.3 | 22.6 |
| Zn2+, total | g | 0.0964 | 0.3214 |
| [Zn2+], (in Total Batch Mass) | ppm | 0.9 | 3.1 |
| Cl −, total | g | 0 | 0 |
| [Cl −], (in Total Batch Mass) | ppm | 0.0 | 0 |
| Na+, total | g | 19.00 | 18.06 |
| [Na+], (in Total Batch Mass) | ppm | 175 | 176 |
| PEG (in Total Batch Mass) | % | 75.5 | 56.5 |
| Water (in Total Batch Mass) | % | 22.1 | 39.0 |

TABLE 2

FORMULA CALCULATOR SPRAY, IMPROVED WOUND COVERAGE

| Component | Units | OINTMENT | SPRAY |
|---|---|---|---|
| Water | kg | 24.00 | 40.00 |
| Water | kg | | |
| H3Cit | kg | 0.20 | 0.20 |
| K3Cit•H2O | kg | 2.15 | 2.15 |
| KCl | kg | 0.00 | 0.00 |
| KOH (as needed for pH) | kg | 0.00 | 0.00 |
| RbC2H3O2 | g | 10.00 | 9.00 |
| Ca3Cit2•4H2O | g | 0.65 | 0.65 |
| Zn3Cit2•2H2O | g | 0.30 | 1.00 |
| Na3Cit•2H2O | g | 81.00 | 77.00 |
| Benzoic Acid | g | 120.00 | 120.00 |
| PEG 400 | kg | 37.00 | 27.00 |
| PEG 4000 | kg | 45.00 | 31.00 |
| WOUND COVERAGE AID | | TBD | TBD |
| Total Batch Mass (calculated) | kg | 108.56 | 100.56 |
| Total Batch Volume (estimated) | L | 30 | 30 |
| K+, total | g | 777 | 777 |
| [K+], (in Total Batch Mass) | ppm | 7161 | 7731 |
| Rb+, total | g | 5.91 | 5.32 |
| [Rb+], (in Total Batch Mass) | ppm | 54 | 53 |
| Ca2+, total | g | 0.1370 | 0.1370 |
| [Ca2+], (in Total Batch Mass) | ppm | 1.3 | 1.4 |
| Zn2+, total | g | 0.0964 | 0.3214 |
| [Zn2+], (in Total Batch Mass) | ppm | 0.9 | 3.2 |
| Cl −, total | g | 0 | 0 |
| [Cl −], (in Total Batch Mass) | ppm | 0.0 | 0 |
| Na+, total | g | 19.00 | 18.06 |
| [Na+], (in Total Batch Mass) | ppm | 175 | 180 |

All patents, published patent applications, and other references disclosed herein are hereby expressly incorporated by reference in their entireties.

The functions of several elements may, in alternative embodiments, be carried out by fewer elements, or a single element. Similarly, in some embodiments, any functional element may perform fewer, or different, operations than those described with respect to the illustrated embodiment. While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

The invention claimed is:

1. A product made by the process of mixing:
    a pharmaceutically acceptable carrier, wherein said carrier is comprised of water and a water-miscible glycol solvent, and
    an acidic solution made of an active ingredient comprising naturally occurring cations having the capacity to facilitate healing of wounds associated with organic anions, wherein the naturally occurring cations are ions of potassium, rubidium, zinc, calcium and sodium and wherein potassium ranges from 0.64 to 1.55 percent of the product, sodium ranges from 0.016 to 0.019 percent of the product, rubidium ranges from 0.005 to 0.022 percent of the product, calcium ranges from 0.0001 to 0.0025 percent of the product, and zinc ranges from 0.00008 to 0.0003 percent of the product.

2. The product of claim 1 wherein said water-miscible glycol solvent is polyethylene glycol.

3. The product of claim 2 wherein the weight ratio of the pharmaceutically acceptable carrier between water and polyethylene glycol is 3:1.

4. The product of claim 2 wherein the weight ratio of the pharmaceutically acceptable carrier between water and polyethylene glycol is 1:1.

5. The product of claim 1 wherein said organic anions are selected from the group consisting of: acetate, hydrogen citrate, dihydrogen citrate, tribasic citrate, and gluconate ions.

6. The product of claim 1 wherein the pH is adjusted to be between 5-7.

7. A composition comprising a pharmaceutically acceptable carrier and an effective amount of an active ingredient made of organic salts of naturally occurring cations, said cations having the capacity to facilitate healing of wounds, wherein the naturally occurring cations are ions of potassium, rubidium, zinc, calcium and sodium and said potassium ranges from 0.64 to 1.55 percent of the composition, sodium ranges from 0.016 to 0.019 percent of the composition, rubidium ranges from 0.005 to 0.022 percent of the composition, calcium ranges from 0.0001 to 0.0025 percent of the composition and zinc ranges from 0.00008 to 0.0003 percent of the composition and the pH ranges for 5-7.

8. The composition of claim 7 wherein said water-miscible glycol solvent is polyethylene glycol.

9. The composition of claim 8 wherein the weight ratio of the pharmaceutically acceptable carrier between water and polyethylene glycol is 3:1.

10. The composition of claim 8 wherein the weight ratio of the pharmaceutically acceptable carrier between water and polyethylene glycol is 1:1.

11. The composition of claim 7 wherein said organic anions are selected from the group consisting of: acetate, hydrogen citrate, dihydrogen citrate, tribasic citrate, and gluconate ions.

12. A method to dress wounds by applying an effective amount of the product of claim 1 to a subject in need thereof.

13. The method of claim 12 wherein said product is applied as a spray.

14. The method of claim 12 wherein said product is applied as a ointment.

15. A method to dress wounds by applying an effective amount of the composition of claim 7 to a subject in need thereof.

16. The method of claim 15 wherein said composition is applied as a spray.

17. The method of claim 15 wherein said composition is applied as an ointment.

\* \* \* \* \*